United States Patent
Kiene et al.

[11] Patent Number: 5,881,626
[45] Date of Patent: Mar. 16, 1999

[54] ROTARY MICROTOME WITH A CRANK MECHANISM

[75] Inventors: Uwe Kiene, Nussloch; Manfred Biehl, Meckesheim, both of Germany

[73] Assignee: Leica Instruments GmbH, Wetzlar, Germany

[21] Appl. No.: 703,431

[22] Filed: Aug. 26, 1996

[30] Foreign Application Priority Data

Aug. 26, 1995 [DE] Germany .......................... 195 31524.3

[51] Int. Cl.⁶ .................................. B26D 7/06; G01N 1/06
[52] U.S. Cl. .............................. 83/707; 83/731; 83/615; 83/915.5
[58] Field of Search .................. 83/915.5, 707, 83/615, 731, 582, 588, 589

[56] References Cited

U.S. PATENT DOCUMENTS

| | | | |
|---|---|---|---|
| 248,151 | 10/1881 | Elward | 83/707 |
| 3,460,417 | 8/1969 | Johnson | 83/915.5 |
| 3,552,247 | 1/1971 | Pickett | 83/915.5 |
| 3,688,500 | 9/1972 | Chancel | 83/915.5 |
| 3,691,889 | 9/1972 | Forsstrom | 83/915.5 |
| 3,771,405 | 11/1973 | Blum | 83/915.5 |
| 3,828,641 | 8/1974 | Sitte | 83/915.5 |
| 3,926,085 | 12/1975 | Shatzel | 83/915.5 |
| 4,126,069 | 11/1978 | Shimonaka | 83/915.5 |
| 4,479,402 | 10/1984 | Reichel et al. | 83/915.5 |
| 4,495,844 | 1/1985 | Jackson et al. | 83/915.5 |
| 4,505,175 | 3/1985 | Reichel | 83/915.5 |
| 4,516,459 | 5/1985 | Kappl et al. | 83/915.5 |
| 4,594,929 | 6/1986 | Behme et al. | 83/915.5 |
| 4,598,621 | 7/1986 | Weinhold | 83/915.5 |
| 5,161,446 | 11/1992 | Holbl et al. | 83/915.5 |
| 5,461,953 | 10/1995 | McCormick | 83/915.5 |

FOREIGN PATENT DOCUMENTS 33 47 238  2/1985  Germany .

Primary Examiner—M. Rachuba
Assistant Examiner—Sean Pryor
Attorney, Agent, or Firm—Foley & Lardner

[57] ABSTRACT

A rotary microtome includes a crank mechanism for moving an object carriage up and down in a vertical path and a drive mechanism for driving the crank mechanism. The object carriage has a receptacle for a specimen holder. A mass-balancer balances the moveable masses of the microtome. The mass-balancer has a pretensioned, adjustable spring element and a pivotably mounted lever for compensating different inertial forces of the microtome in combination with the spring element. A drawing element connects the lever to the object carriage. The mass-balancer is indirectly connected to the drive mechanism by the drawing element.

14 Claims, 2 Drawing Sheets

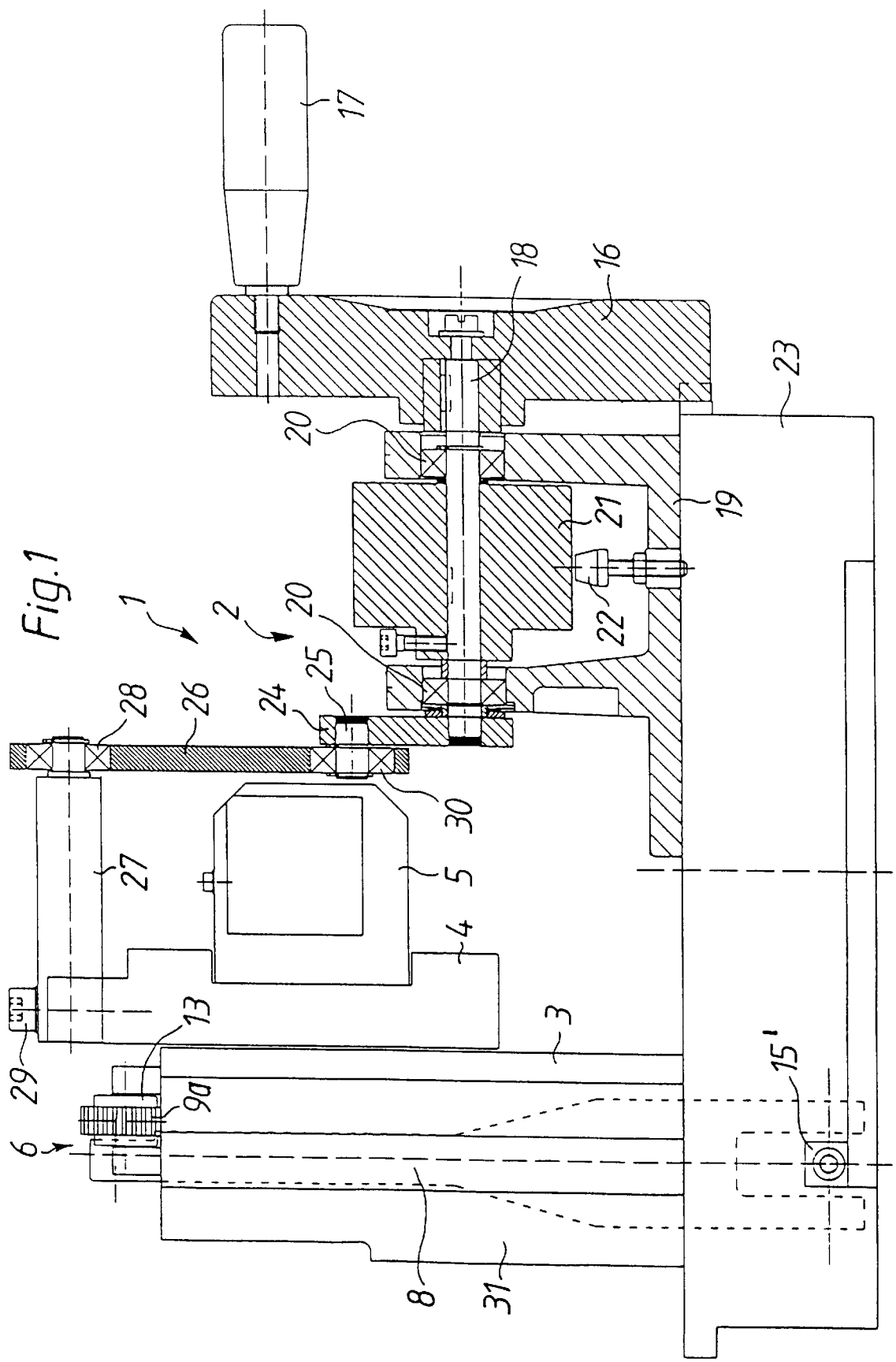

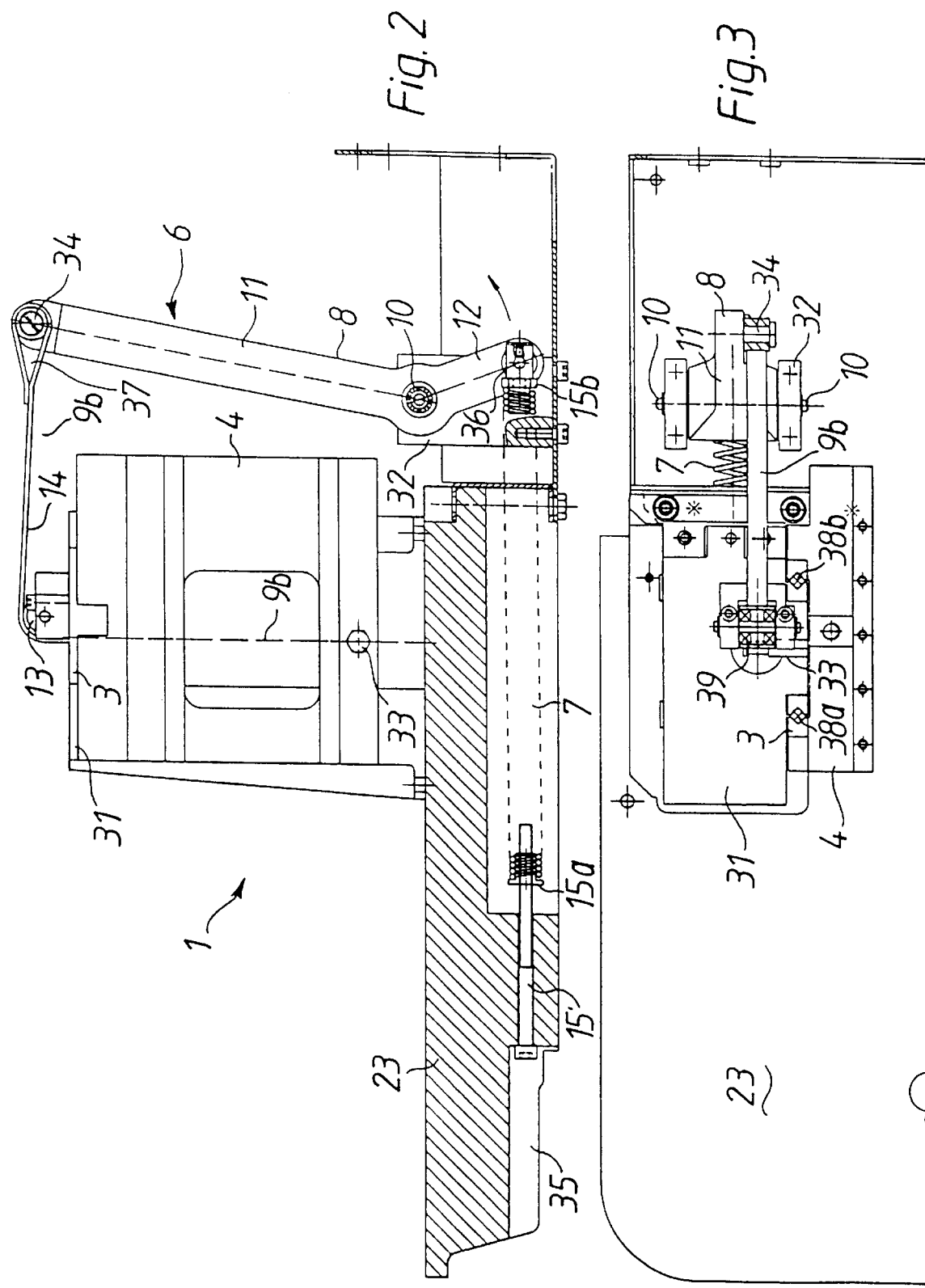

ROTARY MICROTOME WITH A CRANK MECHANISM

BACKGROUND OF THE INVENTION

This invention relates to a novel rotary microtome with a crank mechanism.

A rotary microtome generally includes an object carriage. The object carriage carries a specimen holder that holds a specimen to be cut. The object carriage is moved up and down in a vertical path on the rotary microtome. During this vertical movement, the specimen is passed over a cutter fixedly arranged on the rotary microtome.

In conventional rotary microtomes, control of the vertical cutting movement generally takes place by means of a crank mechanism which is driven by a handwheel. The crank mechanism transforms turning movement of the handwheel into vertical movement of the object carriage. In this type of drive, the moveable masses of the rotary microtome, which includes the specimen and all of the moveable components of the microtome, are alternately and repeatedly accelerated and decelerated. Gravitation accelerates the moveable masses during a first half-turn of the handwheel (downward movement of the object carriage) and decelerates the moveable masses during the second half-turn of the handwheel (upward movement of the object carriage). Thus, only a force reduced by the force of gravitation is required on the handwheel during the downward movement of the object carriage, and a force increased by the force of gravitation is required during the upward movement.

To balance these undesired accelerations and decelerations, rotary microtomes include mass-balancing means. The mass-balancing means generally comprises an asymmetrical balancing weight which is integrated into the handwheel.

Where the moveable masses of the rotary microtome are relatively large, the balancing weight must be dimensioned to be correspondingly large, thereby increasing the bulk of the microtome. Furthermore, an asymmetrically formed balancing weight may produce undesirable vibrations in the rotary microtome during relatively fast upward and downward movements of the object carriage. Vibrations in the microtome inevitably lead to specimens which are uneven and consequently cut in such a way that they are unusable.

DE 33 47 238 C1A discloses a means for dispensing with an asymmetrically formed mass integrated into the handwheel. This document describes a mass-balancing Means which has a cam element fastened on the drive shaft of a crank mechanism. A pivotably mounted lever is positioned on the cam element. A spring element produces the compressive force of the pivotably mounted lever. The torque produced by the lever is dependent on the respective position of the cam element. The torque produced by the lever is inversely proportional to the torque of the microtome's moveable masses at every position of the crank mechanism. Consequently, the handwheel can be actuated uniformly over its entire turning angle.

It has been found in practice, however, that, here too, the microtome vibrates. The cam element causes vibrations during relatively fast cutting movements so that smooth and even cuts can be produced only at a relatively slow drive speed.

The difficulties suggested in the preceding are not intended to be exhaustive but rather are among many which and to reduce the effectiveness of prior rotary microtomes. Other noteworthy problems may also exist; however, those presented above should be sufficient to demonstrate that such apparatuses appearing in the past will admit to worthwhile improvement.

Accordingly, it is therefore a general objective of the invention to provide a rotary microtome which will obviate or minimize difficulties of the type previously described.

It is a specific object of the invention to provide a rotary microtome having a microtome drive that produces no vibrations in the microtome, even at relatively high drive speeds or cutting speeds.

SUMMARY OF THE INVENTION

A preferred embodiment of the invention which is intended to accomplish at least some of the foregoing objects includes a rotary microtome which has a crank mechanism. An object carriage mounted to the crank mechanism has a receptacle for a specimen holder. The rotary microtome also has drive means for driving the crank mechanism to move the object carriage up and down in a vertical path. A mass-balancing means balances the moveable masses of the microtome. The mass-balancing means includes a pretensioned, adjustable spring element and a pivotably mounted lever that compensates the different inertial forces of the rotary microtome in combination with the spring element. A drawing means connects the lever to the object carriage. The mass-balancing means is mechanically connected to the drive means in an indirect manner by the drawing means.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

FIG. 1 is a front detailed view, in partial cross section, and shows a rotary microtome with a crank mechanism in accordance with a preferred embodiment of the invention;

FIG. 2 is a side view of the rotary microtome of the present invention with a mass-balancing means; and FIG. 3 is a top plan view of the rotary microtome of the present invention with the mass-balancing means.

DETAILED DESCRIPTION OF THE PREFERRED EMBODIMENTS

Referring now to the drawings, wherein like numerals indicate like parts, and initially to FIG. 1, there will be seen a rotary microtome 1 with a crank mechanism 2 for moving an object carriage 4 up and down a vertical guide path 3. A handwheel 16 with a handle 17 is provided for driving the crank mechanism 2 and the object carriage 4. The handwheel 16 is connected to a drive shaft 18. The drive shaft 18 is rotatably mounted to a bearing block 19 by two ball bearings 20. The bearing block 19 is fixedly connected to a base frame 23 of the rotary microtome 1. In the region of the bearing block 19, the drive shaft 18 has a symmetrical flywheel 21 for stabilizing the concentricity properties that occur due to an increased mass moment of inertia. For triggering a braking action or arresting the overall drive motion of the microtome 1, a brake 22 connected to the base frame 23 is associated with the flywheel 21.

The end of the drive shaft 18 located opposite the handwheel 16 is fixedly connected to one end of a crank arm 24. A crank pin 25 is fixedly mounted to an opposite end of the crank arm 24 and connects the crank arm 24 to one end of a connecting rod 26. The crank pin 25 is connected to the connecting rod 26 by a ball bearing 30. A second crank pin 27 is mounted to the other end of the connecting rod 26 by another ball bearing 28. This second crank pin 27 is fixedly connected to the object carriage 4 by a screw joint 29.

A specimen holder 5 for receiving a specimen to be cut is detachably fastened to the object carriage 4. The object carriage 4 is arranged to move along the vertical guide path 3 on a frame 31.

When the handwheel 16 is turned by moving the handle 17, that turning movement is transmitted to the object carriage 4 via elements of the crank mechanism 2, including the drive shaft 18, the crank arm 24, the connecting rod 26, and the crank pin 27. Movement of the crank mechanism 2 moves the object carriage 4 up and down along the vertical path 3.

The moveable masses of the rotary microtome 1 are alternately and repeatedly accelerated and decelerated. The moveable masses include the specimen, which, in some cases, weighs only a few grams, and all of the moveable components of the microtome 1, such as the crank mechanism 2, the object carriage 4, the handwheel 16, and the flywheel 21. Together these components may weigh several kilograms. During the first half-turn of the handwheel 16, which causes downward movement of the object carriage 4, the moveable masses are accelerated by gravitation. Then, during the second half-turn of the handwheel 16, which causes upward movement of the object carriage 4, the moveable masses are decelerated by gravitation.

These unequal forces acting on the handwheel 16 are balanced virtually completely by the mass-balancing means 6 of the present invention. To balance these forces, a lever 8 is arranged on a base frame 23 behind the frame 31 for the object carriage 4. A rotatably mounted deflecting roller or pulley 13 is arranged on the frame 31. The deflecting roller 13 includes a ball bearing assembly 39, as shown in FIG. 3. A drawing means 9b runs over the deflecting roller 13. The drawing means 9b is articulated around one end of the lever 8 and is mounted to the top of the object carriage 4, as shown in FIG. 2. The drawings means 9b is fastened to a suspension 33 provided on the object carriage 4, as shown by the dashed lines in FIG. 2.

In the embodiment shown in FIG. 1, the drawing means 9a comprises a toothed belt. The belt 9a preferably is rubber with a steel wire embedded in, or otherwise mounted to, the rubber for reinforcement. The belt's smooth back surface 14 runs over the deflecting roller 13. Suitable drawing means 9a or 9b include toothed belts, ropes, or link chains. The drawing means 9a and 9b must, however, meet the prerequisite of tensile strength and must not allow any elongation.

A spring element 7 is disposed at the other end of the lever 8, as shown in FIG. 2. The spring element 7 preferably comprises a tension spring. The tension of the spring element 7 can be adjusted by adjusting a screw-in sleeve having sleeve parts 15a and 15b and cooperating tensioning screw 15'. This screw assembly 15a, 15b, and 15' is set such that, when the object carriage 4 is in an upper position, there is a tensile stress of adequate force for balancing the moveable masses of the microtome.

FIG. 2 shows a side view of the rotary microtome 1 with the mass-balancing means 6 in accordance with a preferred embodiment of the invention. The lever 8 is pivotably mounted by a pivot pin 10 on a bearing block 32. The lever 8 has, extending from this pivot pin 10, an upper lever arm 11 and a lower lever arm 12. The drawing means 9b is fastened at the end of the upper lever arm 11 by a roller 34. The spring element 7 is connected to an end of the lower lever arm 12 by a pin connection 36. The two lever arms 11 and 12 are designed so that they are angled with respect to each other. The angling of the shorter, lower lever arm 12 with respect to the direction of the upper lever arm 11 has special significance, as will be described further below.

In FIG. 2, the spring element 7 is represented by dashed lines in the region of the frame 23. The spring element 7 is provided at both ends with screw-in sleeve parts 15a and 15b. The pin connection 36 to the lower lever arm 12 is screwed into a sleeve at one end of the spring element 7. A tensioning screw 15', with which the pretensioning of the spring element 7 can be set, is provided at the spring element's other end. The base frame 23 is provided with a clearance 35 in the region of the tensioning screw 15' to allow an operator to access and adjust the screw 15'. The clearance 35 enables an operator to set and adjust the tension of the spring element 7 even during operation of the microtome 1. Readjustment of the spring tension may be necessary if, for example, the moveable masses of the crank mechanism 2 are altered or the specimen holder 5 is changed.

As explained above, the drawing means 9a or 9b is connected by a loop 37 to the roller 34 and, in a preferred embodiment, comprises a toothed belt (see FIG. 1). The toothed belt has a smooth rear surface 14 that runs over a deflecting roller 13 and is connected to the object carriage 4 by the suspension 33.

The lever 8 thus is not directly connected to the crank mechanism 2. Rather, the lever 8 is connected to the crank mechanism 2 only by the suspension 33 of the drawing means 9a or 9b on the object carriage 4. When the object carriage 4 is in an upper position, the tension spring 7 is already tensioned to compensate for the force of gravitation corresponding to the mass of the object carriage. If the object carriage 4 is moved downward, the lower lever arm 12 pivots out in the direction of the arrow. At the same time, the tension spring 7 is further tensioned. The length of the lower lever arm 12 which effects spring tensioning is thereby shortened, so that the product of the effective lever arm 12 and spring force remains virtually constant. It is evident that suitable shortening of the effective lever arm 12 in this case depends on the angular position of the lever arm 12 with respect to the longer, upper lever arm 11. During upward movement of the object carriage 4, the effective lever arm 12 is lengthened and the spring force decreases.

The angular arrangement of the two lever arms 11 and 12 further makes it possible for the dead centers of the two arm positions not to coincide with the upper and lower end positions of the object carriage 4. The forces acting on the crank mechanism 2, and on the object carriage 4, in these end positions are added to equal approximately zero by virtue of the angular arm positions and the increasing and decreasing tensile force of the spring element 7, as appropriate.

FIG. 3 shows a top plan view of the microtome 1 with the mass-balancing means 6. The lever 8 is fastened together with the roller 34 by the pivot pin 10 in the bearing block 32. The lever 8 is connected at the suspension 33 to the object carriage 4 by the drawing means 9. Linear roller bearings, or cross roller guides, 38a and 38b is positioned between the vertical guide path 3 and the object carriage 4.

After reading and understanding the foregoing inventive rotary microtome, in conjunction with the drawings, it will be appreciated that several distinct advantages of the subject invention are obtained.

The rotary microtome is designed so that the mass-balancing means is mechanically connected to the drive means in an indirect manner by the drawing means. The spring element of the mass-balancing means is further indirectly connected to the drive means by the lever. A principle of the invention is that the constant force of gravitation produced by the mass of the vertical carriage is counteracted by an equally large force of the lever-spring system. The handwheel does not contribute to the balance of masses. By dispensing with an eccentrically acting mass on the handwheel, no vibrations are transmitted from the handwheel to the microtome at relatively high cutting speeds.

In a preferred embodiment, the lever is equipped with two lever arms arranged at an angle with respect to each other. The forces acting on the object carriage can be adapted appropriately in all positions by the leverages provided by the lever arms and the tension spring acting on the lower lever arm.

Variable mass ratios in the microtome can be balanced by adjusting the pretensioning of the tension spring. Consequently, it is simple to exchange the specimen holder shown in FIGS. 1–3 for a specimen holder for flat preparations, cartridges, and the like.

By virtue of the adjustable tension spring and the special design of the lever, a variable force is exerted on the object carriage and specimen holder. This variable force, which is dependent upon the position of the crank mechanism, produces a variable torque in the mass-balancing means. The variable torque of the mass-balancing means is superposed on the torque of the moveable masses. The resulting overall torque is constant over the entire turning angle.

This arrangement makes it possible for the object carriage to be brought to a standstill in every position along its path of movement when no additional accelerating forces are acting on it. For example, when changing a preparation, the object carriage does not inevitably drop to its lower stop position. The object carriage may be held at any position. Consequently, the risk of injury to an operator due to an uncontrolled carriage movement, such as a sudden, vertical drop, decreases.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A rotary microtome comprising:

a crank mechanism;

an object carriage mounted to said crank mechanism and having a receptacle for a specimen holder;

drive means for driving said crank mechanism to move said object carriage up and down in a vertical path;

mass-balancing means for balancing moveable masses of said microtome, said mass-balancing means having a pretensioned, adjustable spring element and a pivotably mounted lever for compensating different inertial forces in combination with said spring element;

drawing means for connecting said lever to said object carriage, said mass-balancing means being indirectly connected to said drive means by said drawing means; and a deflecting roller mounted to a frame along which said object carriage travels up and down, wherein said drawing means runs over said deflecting roller.

2. A rotary microtome as claimed in claim 1, wherein said lever has a unitary construction and has two lever arms arranged at an angle with respect to each other about a pivot pin.

3. A rotary microtome as claimed in claim 1, wherein said drawing means is positioned at one end of said lever and said spring element is positioned at an other end of said lever.

4. A rotary microtome as claimed in claim 2, wherein said drawing means is positioned at one end of said lever and said spring element is positioned at an other end of said lever.

5. A rotary microtome comprising:

a crank mechanism;

an object carriage mounted to said crank mechanism and having a receptacle for a specimen holder;

a drive mechanism for driving said crank mechanism to move said object carriage up and down in a vertical path;

a frame having a vertical guide path along which said object carriage moves and a deflecting roller;

a mass-balancer for balancing moveable masses of said microtome, said mass-balancer having a pretensioned, adjustable spring element and a pivotably mounted lever for compensating different inertial forces in combination with said spring element; and a drawing element for connecting said lever to said object carriage, said drawing element running over said deflecting roller, and said mass-balancer being indirectly connected to said drive mechanism by said drawing element.

6. A rotary microtome comprising:

a crank mechanism;

an object carriage mounted to said crank mechanism and having a receptacle for a specimen holder;

a drive mechanism for driving said crank mechanism to move said object carriage up and down in a vertical path;

a mass-balancer for balancing moveable masses of said microtome, said mass-balancer having a pretensioned, adjustable spring element and a pivotably mounted lever for compensating different inertial forces in combination with said spring element; and a toothed belt for connecting said lever to said object carriage, said mass-balancer being indirectly connected to said drive mechanism by said toothed belt.

7. A rotary microtome comprising:

a crank mechanism;

an object carriage mounted to said crank mechanism and having a receptacle for a specimen holder;

drive means for driving said crank mechanism to move said object carriage up and down in a vertical path;

mass-balancing means for balancing moveable masses of said microtome, said mass-balancing means having a pretensioned, adjustable spring element and a pivotably mounted lever for compensating different inertial forces in combination with said spring element; and a toothed belt for connecting said lever to said object carriage, said mass-balancing means being indirectly connected to said drive means by said toothed belt.

8. A rotary microtome as claimed in claim 7, further comprising a deflecting roller mounted to a frame along which said object carriage travels up and down, wherein said toothed belt has a smooth surface which runs over said deflecting roller.

9. A rotary microtome as claimed in claim 1, wherein said spring element comprises a tension spring.

10. A rotary microtome as claimed in claim 1, wherein said spring element is fixed at one end to said lever by a screw-in sleeve and at an other end to a base frame by a screw-in sleeve.

11. A rotary microtome as claimed in claim 10 and further comprising a tensioning screw mounted in said base frame, said tensioning screw cooperating with said screw-in sleeve at said other end of said spring element to adjust tensioning of said spring element.

12. A rotary microtome as claimed in claim 11, wherein said tensioning screw for adjusting tensioning of said spring element is accessible via a clearance in said base frame.

13. A rotary microtome comprising:

a crank mechanism;

an object carriage mounted to said crank mechanism and having a receptacle for a specimen holder;

drive means for driving said crank mechanism to move said object carriage up and down in a vertical path;

mass-balancing means for balancing moveable masses of said microtome, said mass-balancing means having a pretensioned, adjustable spring element and a pivotably mounted lever for compensating different inertial forces in combination with said spring element; and a rope for connecting said lever to said object carriage, said mass-balancing means indirectly connected to said drive means by said rope.

14. A rotary microtome comprising:

a crank mechanism;

an object carriage mounted to said crank mechanism and having a receptacle for a specimen holder;

drive means for driving said crank mechanism to move said object carriage up and down in a vertical path;

mass-balancing means for balancing moveable masses of said microtome, said mass-balancing means having a pretensioned, adjustable spring element and a pivotably mounted lever for compensating different inertial forces in combination with said spring element; and a link chain for connecting said lever to said object carriage, said mass-balancing means being indirectly connected to said drive means by said link chain.

* * * * *